(12) United States Patent
Jenkins, III

(10) Patent No.: US 10,731,690 B2
(45) Date of Patent: Aug. 4, 2020

(54) COUPLING DEVICE AND SMART FABRIC SYSTEM

(71) Applicant: Arthur L. Jenkins, III, Greenwich, CT (US)

(72) Inventor: Arthur L. Jenkins, III, Greenwich, CT (US)

( * ) Notice: Subject to any disclaimer, the term of this patent is extended or adjusted under 35 U.S.C. 154(b) by 32 days.

(21) Appl. No.: 14/438,560

(22) PCT Filed: Oct. 25, 2013

(86) PCT No.: PCT/US2013/066753
§ 371 (c)(1),
(2) Date: Apr. 24, 2015

(87) PCT Pub. No.: WO2014/066729
PCT Pub. Date: May 1, 2014

(65) Prior Publication Data
US 2015/0285287 A1    Oct. 8, 2015

Related U.S. Application Data

(60) Provisional application No. 61/718,362, filed on Oct. 25, 2012.

(51) Int. Cl.
*F16B 17/00* (2006.01)
*A61F 5/02* (2006.01)
(Continued)

(52) U.S. Cl.
CPC .......... *F16B 17/00* (2013.01); *A41D 31/0005* (2013.01); *A61B 5/1126* (2013.01);
(Continued)

(58) Field of Classification Search
CPC ....................................................... F16B 17/00
(Continued)

(56) References Cited

U.S. PATENT DOCUMENTS 5,176,106 A    2/1993   Casto et al.
8,551,030 B2   10/2013  Jenkins, III
(Continued)

FOREIGN PATENT DOCUMENTS

| EP | 0807723 A2 | 11/1997 |
| EP | 2185260 A2 | 5/2010 |
| WO | 2012/034561 A2 | 3/2012 |

OTHER PUBLICATIONS

Australian Examination Report Application No. 2019200866 Completed: Nov. 29, 2019 5 pages.

*Primary Examiner* — Brent T O'Hern
(74) *Attorney, Agent, or Firm* — Welsh IP Law LLC

(57) ABSTRACT

An electromagnetic coupling device. The coupling device has a device body and at least one tongue member protruding from the device body. The tongue member has one or more ferro-magnetic engagement means provided thereon. At least one tongue member receiving means is provided on or defined by the device body and at least one electromagnet is provided substantially adjacent the receiving means. The engagement means provided on the tongue member of a second electromagnetic coupling device may be accommodated within the receiving means of the device body. The electromagnet is operable to cause the engagement means of the tongue member of the said second electromagnetic coupling device to substantially resist or prevent movement of the said tongue member within the receiving means.

13 Claims, 12 Drawing Sheets

(51) Int. Cl.
  *A41D 31/00* (2019.01)
  *A61B 5/11* (2006.01)
  *A61F 5/01* (2006.01)
  *A61B 5/00* (2006.01)
  *B32B 3/08* (2006.01)
  *B32B 5/02* (2006.01)

(52) U.S. Cl.
  CPC .............. *A61B 5/6802* (2013.01); *A61F 5/01* (2013.01); *A61F 5/02* (2013.01); *B32B 3/08* (2013.01); *B32B 5/02* (2013.01); *A61B 2562/046* (2013.01); *B32B 2437/00* (2013.01); *B32B 2535/00* (2013.01); *Y10T 403/32098* (2015.01); *Y10T 428/239* (2015.01); *Y10T 428/249921* (2015.04)

(58) Field of Classification Search
  USPC .......................................................... 428/76
  See application file for complete search history.

(56) References Cited

U.S. PATENT DOCUMENTS

| | | |
|---|---|---|
| 8,708,940 B2 | 4/2014 | Jenkins, III |
| 2006/0080812 A1 | 4/2006 | O'Brien et al. |
| 2006/0236509 A1 | 10/2006 | Ausman |
| 2008/0110050 A1* | 5/2008 | Prickell ................ A43B 1/0081 36/50.1 |
| 2010/0055043 A1 | 3/2010 | Moore |
| 2013/0276218 A1* | 10/2013 | Parisi, Jr. .................. F41H 1/02 2/463 |

* cited by examiner

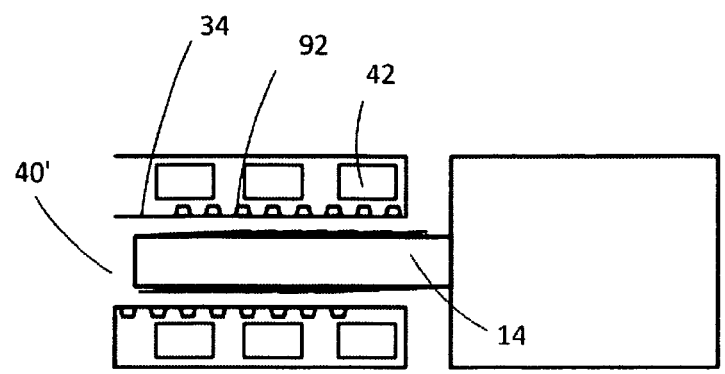
FIG. 9a
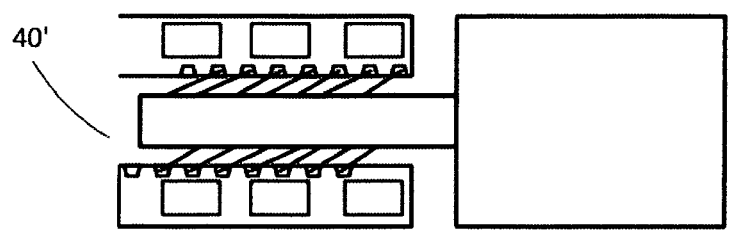
FIG. 9b
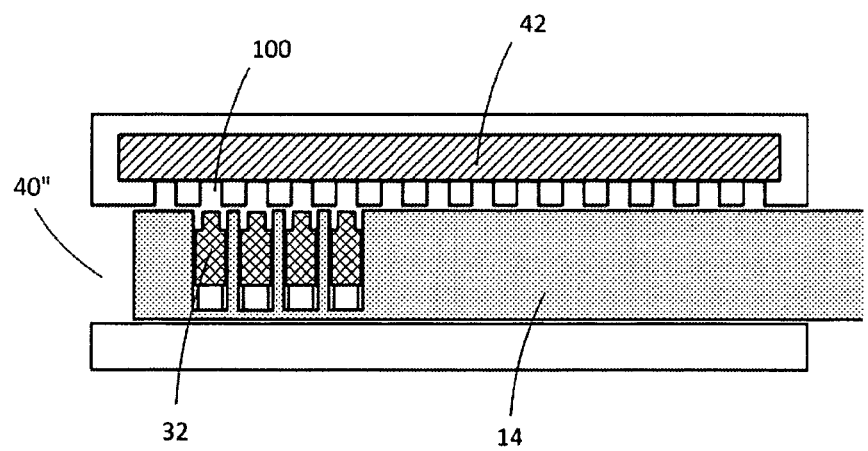
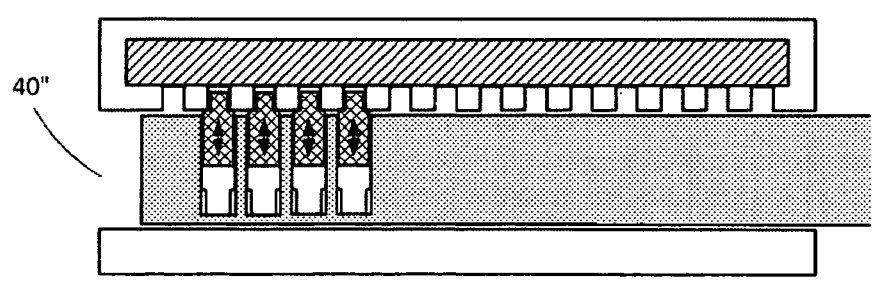
FIG. 10

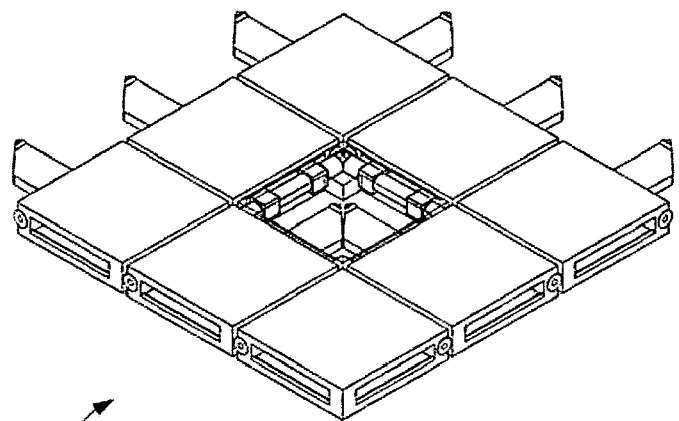
FIG. 15a
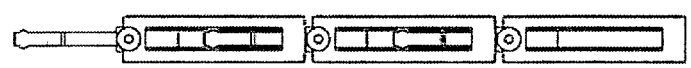
FIG. 15b
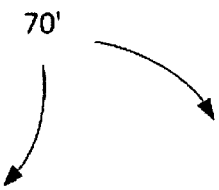
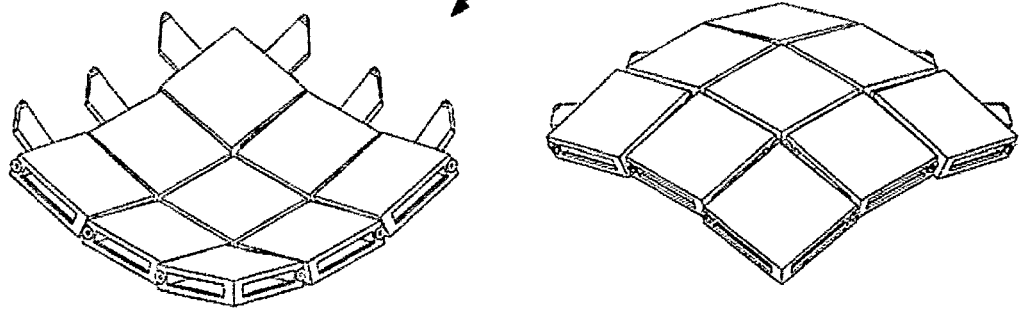
FIG. 15c

COUPLING DEVICE AND SMART FABRIC SYSTEM

The use, operation and application of coupling devices and smart fabrics are relevant, but in no way limited, to the brace devices and spinal support devices disclosed in co-pending U.S. patent application Ser. No. 13/147,231, entitled "Dynamically Reactive Spinal Support System", filed on Aug. 1, 2011 as a National Stage application of PCT/US2010/055043 and claiming priority from U.S. Provisional Patent Application Ser. No. 61/257,793 filed on Nov. 3, 2009, and in co-pending U.S. patent application Ser. No. 13/195,826, also entitled "Dynamically Reactive Spinal Support System", filed on Aug. 1, 2011 as a continuation in part of application Ser. No. 13/147,231; these disclosures are incorporated herein by reference.

BACKGROUND OF THE INVENTION

This invention relates to an electromagnetic coupling device and to a smart fabric formed from the interconnection of a plurality of the coupling devices.

SUMMARY OF THE INVENTION

According to a first aspect of the invention there is provided an electromagnetic coupling device, the coupling device comprising:
  a device body;
  at least one tongue member protruding from the device body, the tongue member having one or more ferro-magnetic engagement means provided thereon;
  at least one tongue member receiving means provided on or defined by the device body; and
  at least one electromagnet provided substantially adjacent the receiving means;
wherein the engagement means provided on the tongue member of a second electromagnetic coupling device may be accommodated within the receiving means of the device body, and wherein the electromagnet is operable to cause the engagement means of the tongue member of the said second electromagnetic coupling device to substantially resist or prevent movement of the said tongue member within the receiving means.

Typically the at least one tongue member is hingedly connected to the device body. Preferably, a textured surface is provided within the tongue member receiving means to provide enhanced frictional contact between the engagement means and the receiving means. Typically, the engagement means are housed within locking recesses provided on the tongue members and biased to remain within the recesses unless the electromagnets are activated. Alternatively, the engagement means may be biased outwardly from the recesses and retracted within the recesses upon activation of the electromagnets.

The resistance or prevention of movement may be selective and/or partial through variation of the magnetic force applied by the one or more electromagnets.

According to a second aspect of the invention there is provided a flexible smart fabric, the smart fabric comprising a plurality of inter-connected electromagnetic coupling devices, wherein the engagement between any two or more coupling devices is selectively and/or partially activated or deactivated in order to render all or one or more portions of the smart fabric in to a substantially flexible or substantially rigid condition.

Generally, the smart fabric is encapsulated within a stretchable fabric material.

One or more sides of coupling devices incorporated in a smart fabric assembly may be tapered or otherwise shaped to facilitate configuration with specific surface contours anticipated in a given application. Moreover, the smart fabric may incorporate electromagnetic coupling devices together with simplified coupling devices that carry engagement means on the tongue members that may operate with interconnected electromagnetic coupling devices, but where the simplified coupling devices do not include electromagnets.

According to a third aspect of the invention there is provided a flexible fabric, the fabric comprising:
  a plurality of interconnected coupling devices, each coupling device having a device body, at least one tongue member protruding from the device body, one or more tongue member receiving means provided on or defined by the device body, wherein the at least one tongue member of a second coupling device may be accommodated within the receiving means of the device body, and wherein the at least one tongue member of the accommodated coupling device is at least partially flexible relative to the device body and/or at least partially moveable within the receiving means; and
  retaining means, provided on the at least one tongue member and/or the one or more receiving means, the retaining means being operable to afford movement of the tongue member in the corresponding receiving means within predefined spacial limits, but preventing the tongue member from decoupling from the receiving means in use; the interconnected coupling devices thereby being separable and rotatable relative to the others within the limits afforded by the retaining means and in combination forming a flexible fabric assembly.

BRIEF DESCRIPTION OF THE DRAWINGS

FIG. 9 shows an alternative embodiment of the engagement means and tongue member receiving means, in the form of hingedly connected ferro-magnetic "bristles";

FIG. 10 shows another alternative embodiment of the engagement means and tongue member receiving means, in the form ferro-magnetic pins locking within holes provided within the recess cavity;

FIG. 13b shows a free moving car corresponding to the device of FIG. 13a;

FIG. 15a shows a smart fabric assembly formed of the alternate electromagnetic coupling devices;

FIG. 15b is a side view of the assembly in FIG. 15a; and

FIG. 15c shows the assembly in FIG. 15a flexed in different orientations.

The illustrations are intended to provide a general understanding of the concepts described and the structure of various embodiments, and they are not intended to serve as a complete description of all the elements and features of methods and systems that might make use of the structures or concepts described herein. Many other embodiments will be apparent to those of skill in the art upon reviewing the description. Other embodiments may be utilized and derived therefrom, such that structural and logical substitutions and changes may be made without departing from the scope of this disclosure. It should also be appreciated that the figures are merely representational, and are not be drawn to scale and certain proportions thereof may be exaggerated, while others may be minimized. Accordingly, the specification and drawings, together with any examples, are to be regarded in an illustrative rather than a restrictive sense and the specific form and arrangement of the features shown and described are not to be understood or interpreted as limiting on the invention.

DESCRIPTION OF EMBODIMENTS

Figure 1:
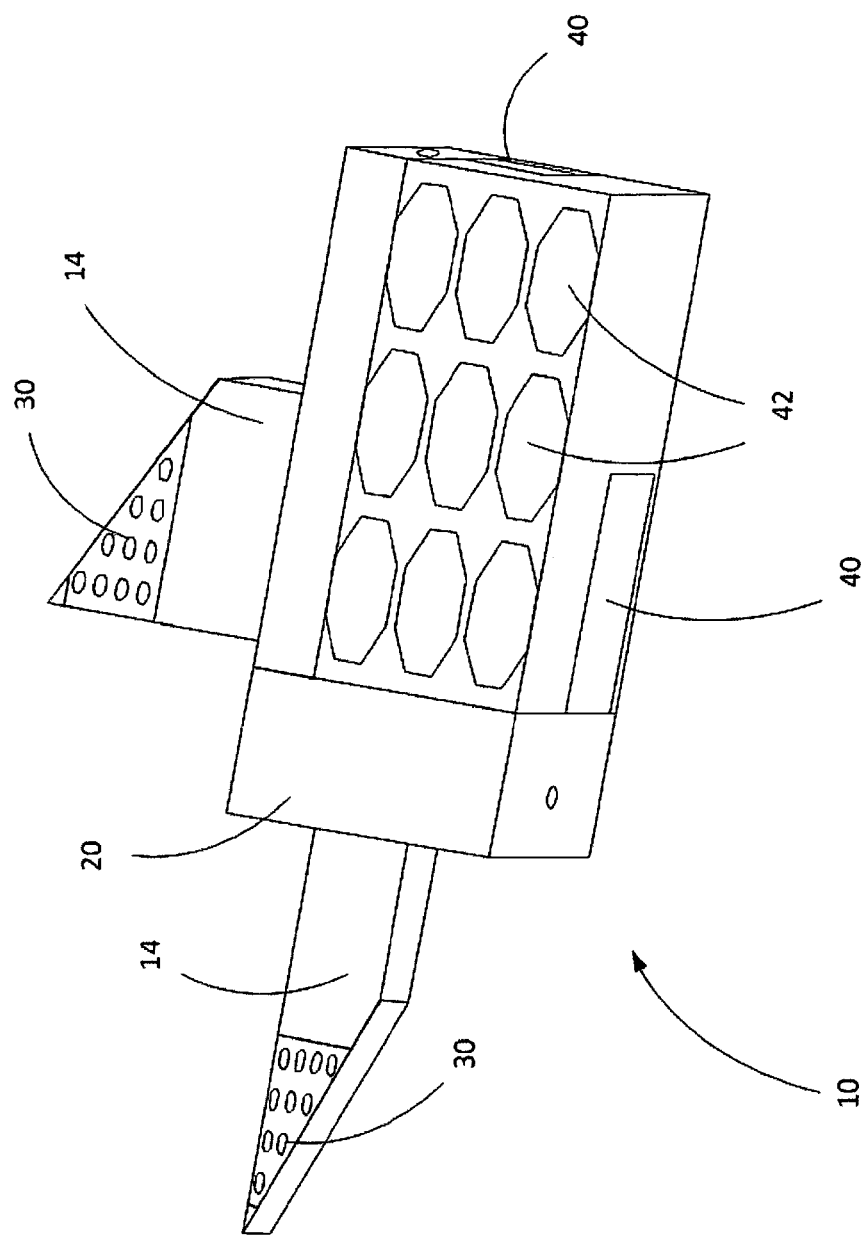
FIG. 1 shows an isometric perspective view of the electromagnetic coupling device of the present invention.
Figure 2:
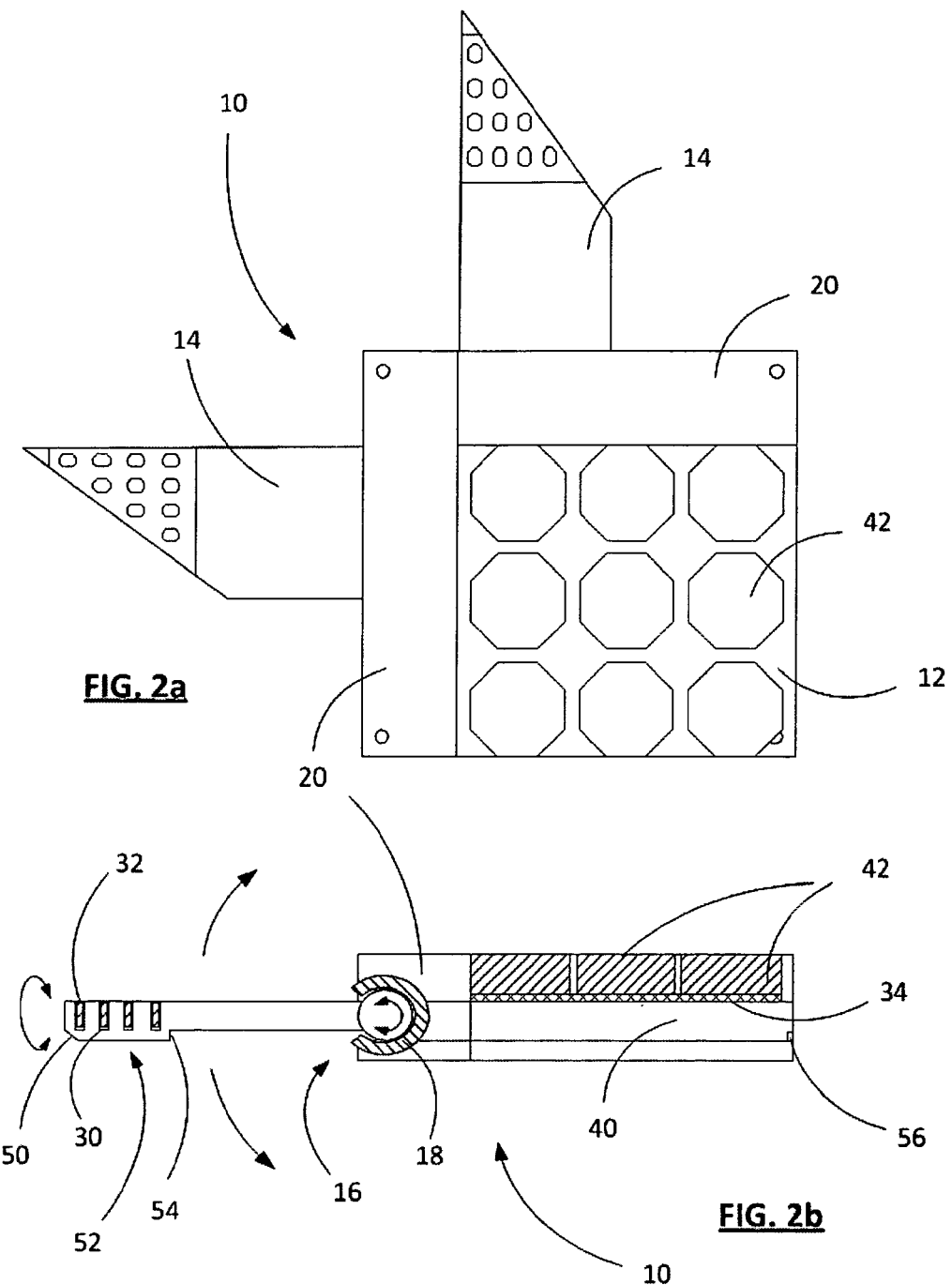
FIGS. 2a and 2b show plan and cutaway side views of the electromagnetic coupling device of FIG. 1.

FIGS. 1 and 2 show a first embodiment of the electromagnetic coupling device 10 of the present invention. The electromagnetic coupling device has a device body 12 and two tongue members 14 protruding from the device body. The device body is preferably manufactured from a ballistic grade plastic or other suitable non-magnetic material, including aluminum and/or magnesium alloys. The device body is preferably also radio-translucent or radio-opaque to substantially facilitate use of X-rays. In the general applications envisaged, the sides of the device body are typically 1 cm square (in top view) or less, and the thickness is less than 0.5 cm; although it should be readily appreciated that the coupling device could be of any appropriate application-dependent size.

The tongue members 14 are connected to the device body through a hinge arrangement 16, comprising a rigid axial cylinder 18 supported within a casing 20. The hinge arrangement enables movement of the tongue members in a first plane (as shown and orientated for vertical movement in FIG. 2b). The range of movement of the tongue members is also defined by edge openings of the axial cylinder of the hinge arrangement. The tongue members are typically formed of a plastic or polymer having some inherent flexibility, thereby also affording limited torsional/rotational movement as indicated in FIG. 2b.

Small locking recesses 30 are provided on an engagement portion located at the distal portion of the tongue members 14; within the locking recesses are provided free moving engagement means, such as ferro-magnetic shear pins 32, which are typically biased to remain within the locking recesses prior to deployment generally with an elastic membrane, spring or elastic tether. For example, a small spring, tether or membrane may be located and attached at the base of the locking recesses and attached to the bottom of the pin. Alternatively, a membrane could be generally positioned and affixed over the engagement portion (where the locking recesses and pins are located) to trap the pins within the locking recesses. A further alternative could position one or more magnets, generally permanent magnets, at the base of the locking recesses to magnetically retain the pins within the recesses.

The device body 12 also defines tongue member receiving means, for example in the form of recess cavities 40, which are adapted to accept the tongue members 14 of other like or similar electromagnetic coupling devices 10. Electromagnets 42 are arranged adjacent (substantially over) the recess cavities; when a tongue member of one electromagnetic coupling device is located within the recess cavity of another, the electromagnet may be electrically activated into a deployed condition, thereby drawing the free moving pins 32 magnetically towards a textured surface 34 provided within the recess cavity.

Figure 3:
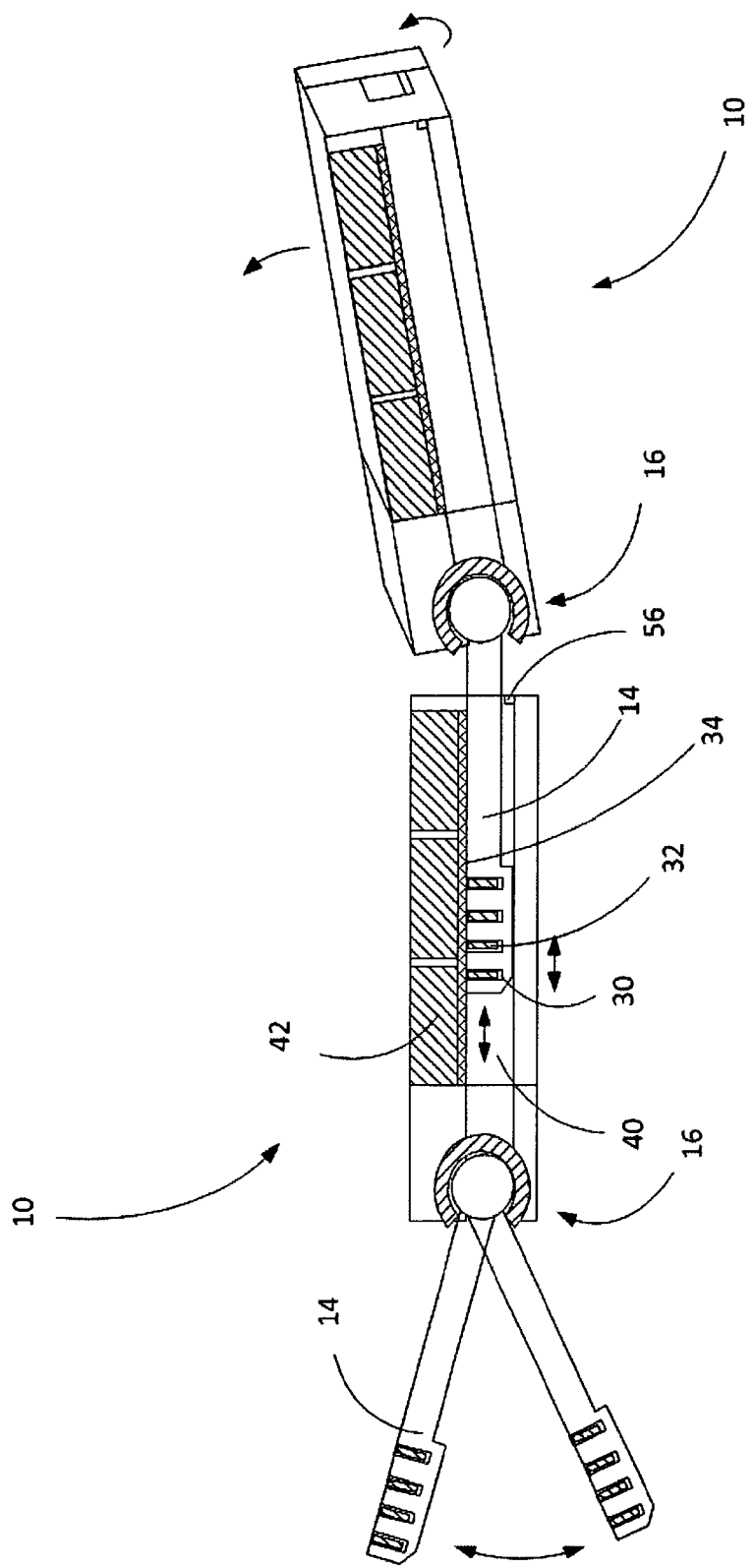
FIG. 3 shows one electromagnetic coupling device of the present invention in engagement with a second like electromagnetic coupling device.
Figure 4:
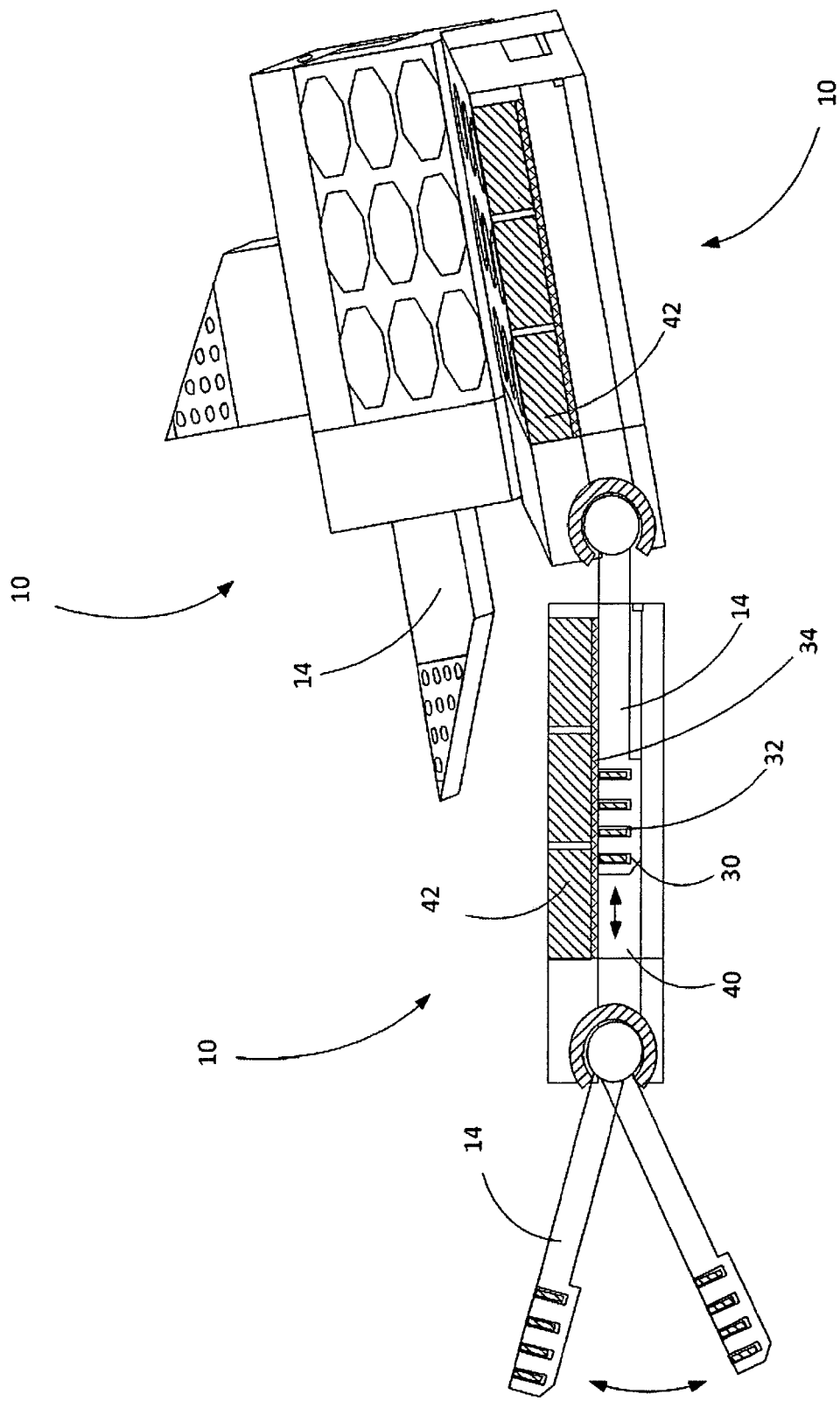
FIG. 4 shows a third electromagnetic coupling device in engagement with the combination of electromagnetic coupling devices in FIG. 3.

In FIG. 3, the tongue member 14 of one electromagnetic coupling device 10 is located within the complemental recess cavity 40 of another electromagnetic coupling device. It should be apparent that the engagement portion of the tongue member is initially freely moveable within the receiving recess cavity and minimal torsional (twisting) of the engaging electromagnetic coupling device and general (upward) movement from the hinge arrangement 16 is evident in the illustrative figure. FIG. 4 extends the illustrative example, additionally providing another receiving electromagnetic coupling device (shown with even more movement in an upward orientation relative to the electromagnetic coupling device with which it is engaged). From FIGS. 3 and 4, it should be evident that a substantial degree of relative movement is possible between the electromagnetic coupling devices.

The position of each tongue member 14 may be locked in place within a complemental recess cavity 40 upon activation of one or more of the electromagnets 42 associated with the recess cavity of the receiving electromagnetic coupling device 10. Upon activation of the electromagnets, the free moving pins 32 are drawn up into engagement with the textured surface 34 with a force sufficient to prevent movement, or to resist movement to a desired extent. The textured surface (and/or the engaging surface of the pins, or the surface membrane if provided) may have a rough (abrasive) surface to facilitate frictional engagement, or alternatively the textured surface may have small holes or dimples provided in the surface to facilitate engagement. The degree of engagement (by selectively varying the magnetic force applied by one or more of the electromagnets on one or more coupling devices, or by activating the electromagnets independently to apply variations in magnetic force) is controlled by a computerized central processing unit (the degree to which the retaining bias of the pin is overcome by the force applied by the electromagnet). Where a membrane is used to retain the free moving pins 32 in a biased condition within their locking recesses 30, the texture of the membrane may also contribute to the frictional resistance provided against the textured surface 34. Where a permanent magnet is used to retain the pins, the electromagnetic force must clearly be sufficient to overcome the magnetic force holding each pin in place.

It should be appreciated that the free moving pins 32 could also be biased in an outward orientation relative to the locking recesses 30 (so that they are engaged in a deployed condition within the recess cavities 40 unless the electromagnets are activated, repulsing the pins into a retracted position within the locking recesses); thereby causing the configuration of electromagnetic coupling devices to retain a predetermined orientation relative to one another unless the electromagnets are activated to enable reorientation.

In general operational use, a plurality of the inter-connected electromagnetic coupling devices will be assembled in a predefined pattern for a particular purpose; for example, as a lining for a neck brace or helmet. Consequently, the tongue members 14 are required to remain in place within the recess cavities 40; so the tongue members preferably feature a chamfered or beveled leading edge 50 (for ease of insertion within the recess cavities) on a profiled stepped section 52, forming a lip 54 that will abut a corresponding limiting protrusion 56 provided at the outer edge of the recess cavity to prevent disengagement. This can be seen, for example, in FIG. 3.

Figure 5:
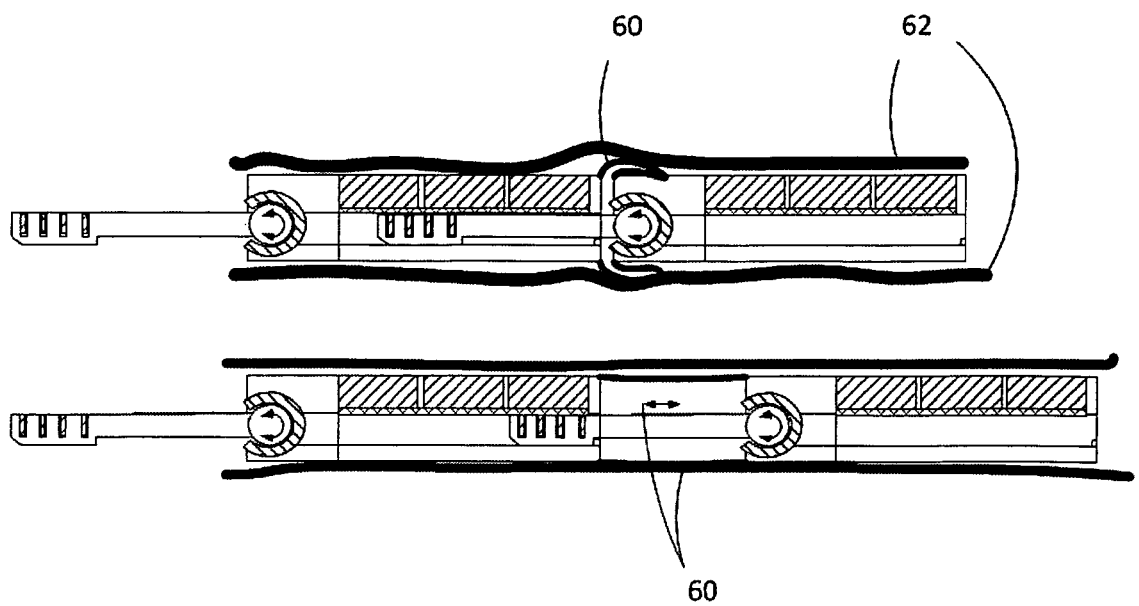
FIG. 5 shows two connected electromagnetic coupling devices of the present invention encapsulated within a fabric material.

Typically the assembly of interconnected electromagnetic coupling devices 10 is held together only in this manner, although additional loosely fitting tethers 60 (see FIG. 5, showing two electromagnetic coupling devices in proximate and extended positions relative to one another) may also be provided to ensure the inter-connectivity is maintained under extreme loading (where the tether is stretched). The assembled devices may also be covered in a flexible (preferably stretchable/elasticated) fabric material 62 (such as Lycra) which may house the wiring or thin metallic sheet micro-connectors (not shown) required to carry electric charge to the electromagnets 42 on the devices (FIG. 5 shows the fabric overlapping the devices). The assembly, when configured in this manner, functions as a smart fabric. The assembly and/or covering material may also house appropriate batteries, computer processing functionality and sensors required for operation of the assembly.

Figure 6:
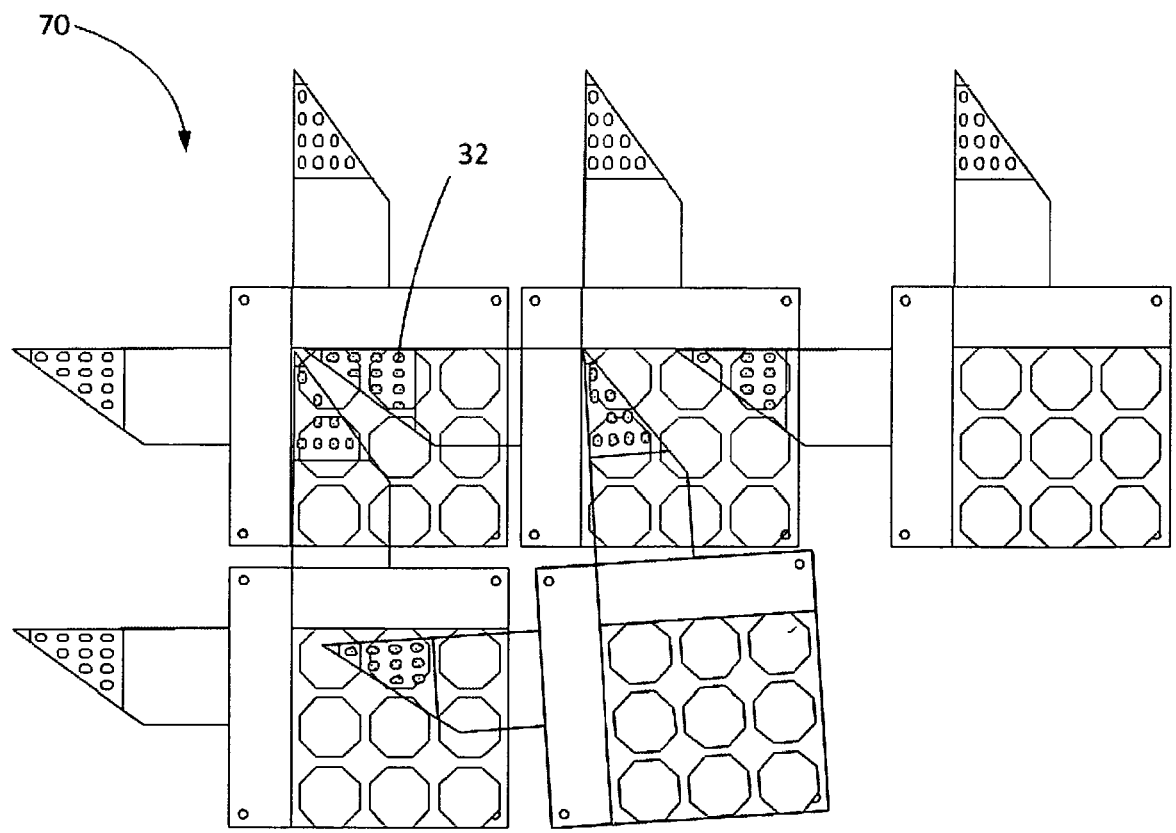
FIG. 6 shows a number of electromagnetic coupling devices connected together to form a smart fabric as contemplated in the present invention.
Figure 7A:
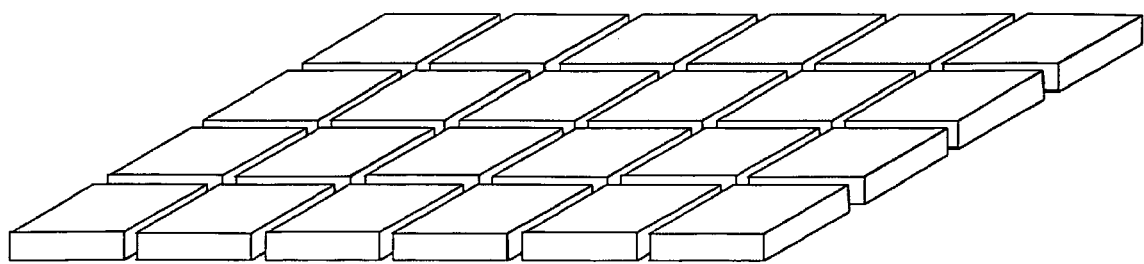
FIGS. 7a and 7b show in simplified form a number of inter-connected electromagnetic coupling devices in a flat smart fabric configuration and flexible configuration respectively.
Figure 7B:
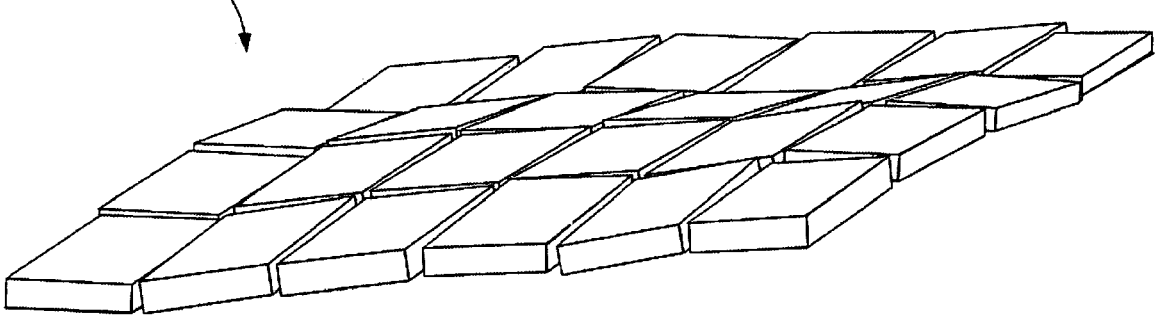
Figure 8:
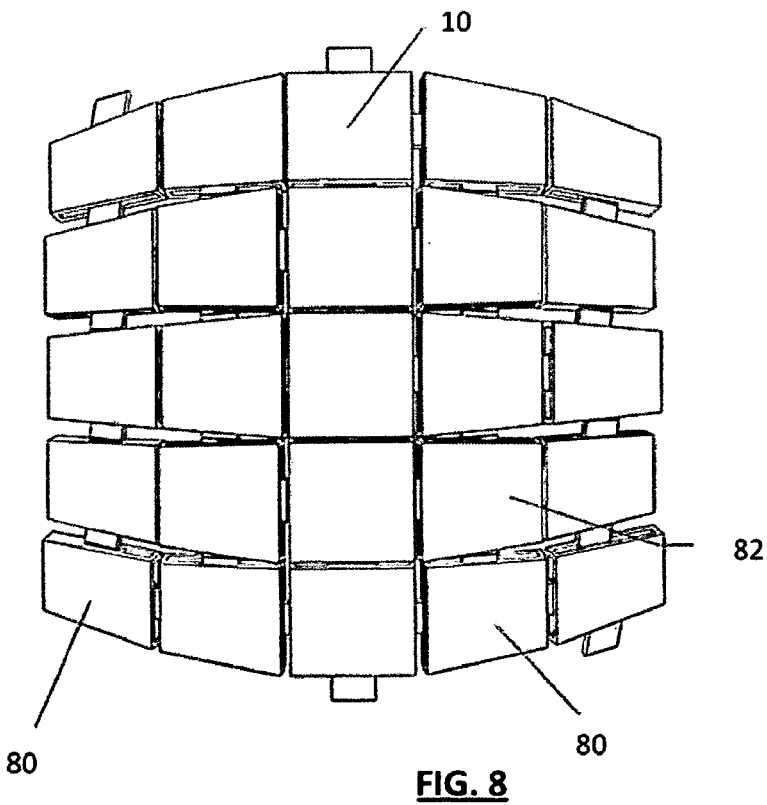
FIG. 8 shows a smart fabric assembly where some of the electromagnetic coupling devices have one or more sides.

FIG. 6 shows a number of electromagnetic coupling devices being connected together to form a smart fabric 70 (and also indicating that only certain free moving pins 32 are engageable with the textured surface 34 for any given configuration by virtue of the positioning of the electromagnets 42. FIG. 7a shows, in a simplified graphic form, a number of inter-connected electromagnetic coupling devices in a flat configuration and FIG. 7b shows some flexibility of the assembly, which can be completely, partially or selectively "crystallized" into a fixed configuration upon activation of electromagnets. FIG. 8 shows an assembly, where some of the electromagnetic coupling devices are not square in plan perspective, but have tapered sides (on one or both sides) which enable the assembly to define an anticipated contoured surface more accurately (for example, within a helmet). It should be apparent that the tapering can be varied on one side 80 or more sides 82 as needed for any given application. It should also be appreciated that the sides of the coupling devices can be otherwise shaped as appropriate to facilitate surface contouring and certain coupling devices may only have one tongue member (at the edges of a smart fabric assembly, for example). Furthermore, some coupling devices may be partially or totally magnetically inoperable; being flexible or rigidly connected in one or more orientations at all times relative to other devices. Such simplified coupling devices may be utilized either only with other simplified coupling devices, or in combination with electromagnetic coupling devices; typically simplified coupling devices being positioned at places where free or restricted movement is required at all times or where flexibility/rigidity is not relevant (and not warranting use of electrical energy to activate/deactivate the coupling devices). Alternatively, the interconnected devices may be positioned once, and then not used in operation again unless manually recalibrated (such as the snug fitting of less critical areas around a wearer's body).

Other means for locking the tongue members 14 within the recess cavities 40 are obviously possible. An alternate embodiment, for example, is shown in simplified form in FIG. 9, where engagement means in the form of hingedly connected ferro-magnetic "bristles" 90 are utilized; these may be deployed or retracted upon activation/deactivation of the electromagnets 42 (biasing options in extended and retracted configurations remain as described above). When caused to stand proud, the bristles engage in holes/dimples 92 located on the textured surface 26 (the bristles do not tangle as they are too long to stand up completely). It can be seen from the illustrative figures that in this embodiment, there are two electromagnetically activated textured surfaces provided in the tongue member engagement means (recess cavity 40') and the bristles on one side engage in a different direction to those on the other side (thereby resisting/preventing movement in both directions within the recess cavity). The bristles are preferably formed from a memory metal, so that they instantaneously jump to a preconfigured state.

The bristles may also be controlled by various means other than electromagnetic means. The bristles could be manipulated mechanically into or out of engagement; for example, the bristles could be pulled up into engagement in manner similar to a model ship being raised into position within a glass bottle. Flexible yarn or string might be attached to the bristles on the tongue member side and on the recess cavity side, such that movement of the tongue relative to the recess cavity causes tension in the yarn/string and raises the bristles into engagement. Utilizing simple pulleys or guides, movement in or out of the recess cavity can be controlled to effect engagement or disengagement as appropriate for the application. It should be apparent that many other means of effecting movement of the bristles are possible and these might include the use of substantially rigid operating arms/rods driven by mechanical, pneumatic, hydraulic or other means.

In another alternate locking embodiment, see FIG. 10, the ferro-magnetic pins 32 of the tongue member 14 lock within holes 100 provided within the recess cavity 40" (not merely engaging against a textured surface). The electromagnet 42 as shown in this instance may be a singular magnet as variations and selective application is not relevant (the devices merely lock or unlock). Again, it will be appreciated that the pins could be engaged or disengaged through means other than magnetic means. Pneumatic or hydraulic compression resistance could be utilized in a manner similar to a shock absorber, for example, resisting movement in response to forces applied (the resistance potentially being in varying degree dependent upon the extent of the force applied). Alternatively, pneumatic or hydraulic displacement could be applied to activate the locking pins against the resistive textured surface; a plunger, for example, could push air, gas or fluid into the space below the pins to push them to the textured surface.

In addition, the tips of the pins 32 shown in FIG. 10 may be conical or rounded; in which event the pins may be displaced back into the substantially retracted position as the tongue member is pulled or pushed within the recess cavity under a sufficient application of force; thereby providing limited resistance to movement. Alternatively, where the pin heads are shaped more like barbs, complete locking of the tongue and cavity is effected and no force (other than very severe force, resulting in complete failure of the interface) will allow the pins to be pushed down and transiently disengage.

Figure 11:
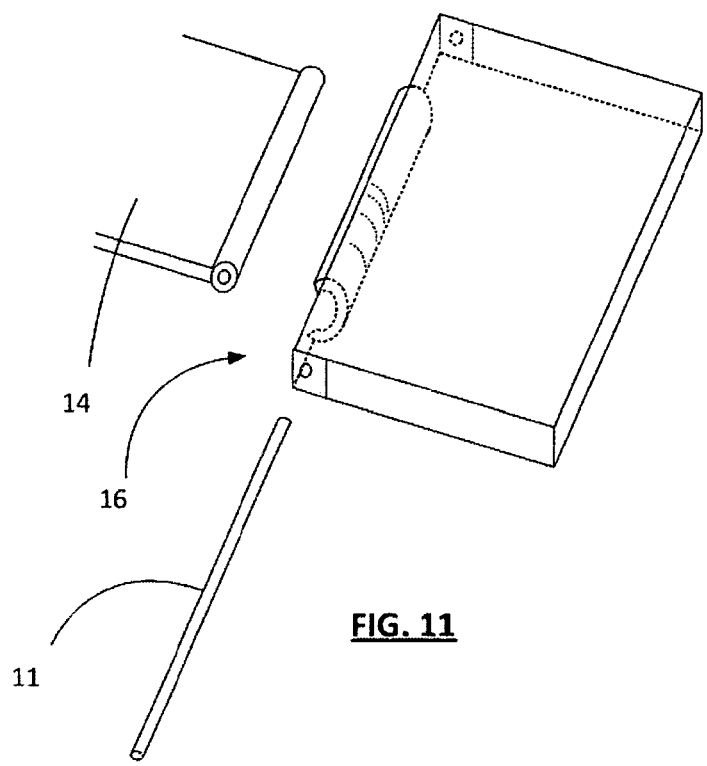
FIG. 11 shows a general exploded view of the hinge assembly.
Figure 12A:
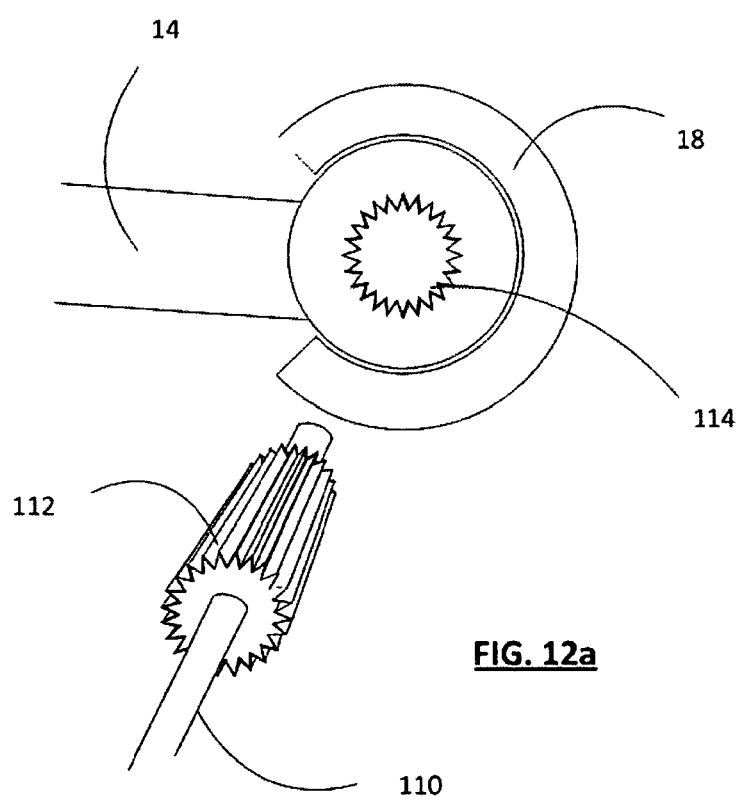
FIGS. 12a and 12b show alternative exemplary locking mechanisms for the hinge assembly.
Figure 12B:
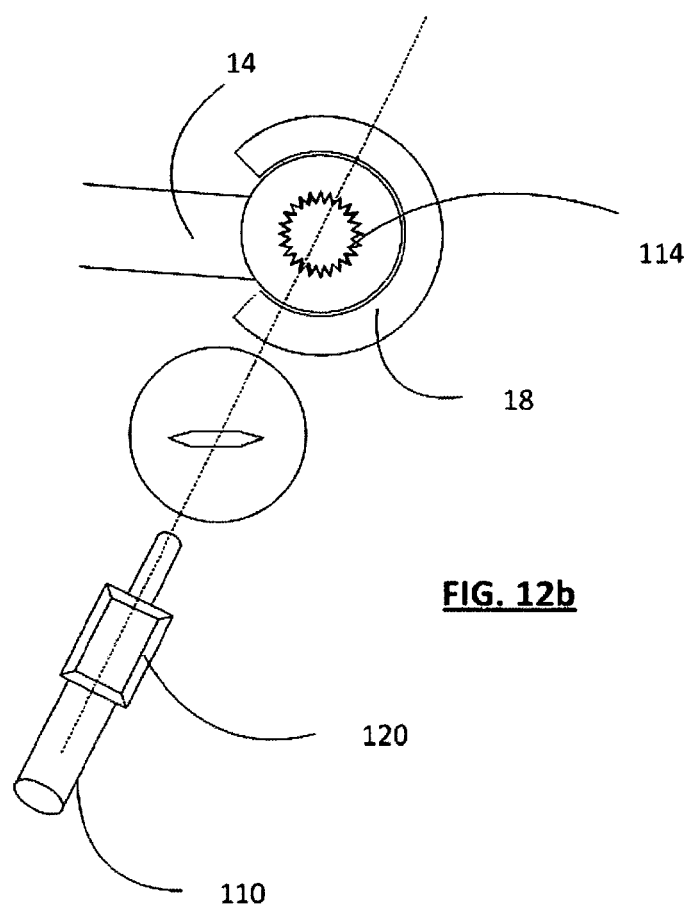

Embodiments for the locking mechanisms for the engagement of the tongue members 14 and recess cavities 40 have been described; restricted movement of the tongue members provides considerable static strength to the assembly of numerous electromagnetic coupling devices. However, in many applications it may be desirable to lock the hinge assembly 16 in place. FIG. 11 shows a general exploded view of the tongue member 14 and hinge assembly, which is held together with an axial retaining rod 110. In one embodiment, see FIG. 12a, the retaining rod carries a tapered, conical toothed/geared ratchet 112 that is axially engageable within a corresponding toothed female cavity 114 provided on the tongue member. The rod and/or ratchet is ferromagnetic, such that the rod and/or ratchet may be moved axially in or out of the cavity to cause engagement or disengagement of the axel within the cavity and thereby locking or releasing the free movement of the hinge assembly. The rod and/or ratchet combination are driven by one or more electromagnets positioned at or towards the end(s) of the rod (not shown) within the casing 20. The rod carrying the ratchet may be a solenoid core within the driving electromagnet with the ratchet fixed to the rod so that the combination are moved in and out of engagement, or the ratchet may be driven on the rod (being magnetically pulled or pushed into or out of engagement), or the rod/ratchet combination may be pulled/pushed by the magnets. In an alternative embodiment, see FIG. 12b, an engagement key 120 is provide on the rod; this too is moveable with or on the rod to provide engagement of the key blades within the female ratchet cavity. A cover plate 122 is also shown in this embodiment that would be interposed between the rod and the ratchet cavity, attached to the electromagnetic coupling device body, to prevent movement.

The invention also contemplates the use of other locking mechanisms for engaging and disengaging the hinge assembly. A viscoelastic substance could be used, for example, that changes its configuration depending on a stimulus, such as an electrical signal or charge, or upon application of force (such as being struck or bent), or by other mechanical or chemical changes. Materials incorporating "memory" materials may return to a predefined configuration that engages or disengages the hinge assembly; or materials with nanotechnology may be generally soft and flexible in normal circumstances, but are able to harden almost instantaneously when subjected to an impact or other external stimulus could be used. In this regard, the Dow Corning Active Protection System is soft, flexible and breathable in normal conditions, but hardens almost instantly upon receiving an impact (and then returns to the flexible state when the impacting force is removed). Also, certain "meta-materials" are also controllable and capable of dynamic activation through various means.

It should also be appreciated that the material used for locking the hinge could react differently to the degree of force being applied. Materials with non-Newtonian fluid properties, for example, have different physical properties when strong or mild forces are applied. In this manner, a wearer of a fabric of the invention might be able to make slow gentle movements, but faster movements would generate increasing resistance. A non-Newtonian liquid within the hinge, such as a gel or fluid within the interface, might be used. Similarly, the hinge joint could be replaced, by connecting the tongue member to the hinge location through a short section of non-linear material, such as Dow Deflexion material, so that it bends with gentle movement but is rigid with the application of increased force through abnormal movement.

A non-Newtonian fluid may also be used in the tongue member/recess cavity interface; for example, the tongue member can act like a plunger in a syringe chamber, where the chamber (recess cavity) is filled with a non-Newtonian fluid. When the tongue member plunger is gently moved in to the recess cavity it moves easily; but if it is moved more forcefully it acts like a solid and will not move. This could be achieved by having a gel within the recess cavity that will not leak out, or by using some other type of fluid-tight seal around the tongue member, or by applying a magnetic barrier that prevents the liquid from leaving because of magnetic particles in the fluid, etc. In any of these circumstances, the tongue member would be resisted by the contents of the recess cavity in a non-linear manner, so that the harder the push the less the movement.

The smart fabric assembly of the present invention can be controlled (selectively activated/deactivated) as needed manually, upon fitment or when a change to the configuration is desirable. Alternatively, the selective activation/deactivation may be automated and programmed to respond according to predetermined parameters. Internal and/or external movement sensing means for determining any external forces being applied to the electromagnetic coupling device assembly (and therefore to the wearer) may be provided. This external force will manifest itself in two ways: causing the assembly to be pushed in one direction (angular movement) as well as a downward (translational) movement. Typically movement sensing means are operated continuously during any activity potentially requiring support from the assembly. Movement sensing means include, but are not necessarily limited to, accelerometers, gyroscopes, force-transducers, pressure sensors, strain gauges and the like. Generally the electromagnetic coupling device assembly will utilize accelerometers and gyroscopes; although the assembly may incorporate any of these or other sensing devices or products.

Gyroscopes can detect variations in the inclination of the assembly, namely pitch and yaw. Accelerometers monitor the magnitude and direction of acceleration (the rate of change in velocity) as a one, two, or three dimensional vector quantity that can detect changes in orientation and the application of shocks. Preferably, the accelerometers utilized are three dimensional (triple-axis) detecting accelerometers, but combinations of these sensors can achieve similar goals. As with presently available airbag deployment mechanisms, accelerometers may be used to detect the rapid negative acceleration (deceleration) thereby determine whether an automated response is appropriate.

These movement sensing means may be deployed externally, being mounted on one or more of the electromagnetic coupling devices, or carried independently, or be linked to another device to which the electromagnetic coupling device assembly is active or associated. For example, a wearer in a vehicle may have a device utilizing the smart fabric assembly that is in communication with the vehicle's airbag sensors and/or the dynamic stability control sensors (controlling vehicle handling in response to cornering and braking forces etc.); where the electromagnetic coupling device smart fabric is activated completely or partially upon certain of the vehicle systems experiencing one or more predetermined conditions. The movement sensing means may also be deployed internally; for example, on one or more of the electromagnetic coupling devices. Modern accelerometers, gyroscopes and other sensing devices are often very small micro electro-mechanical systems (as evidenced by their use in many handheld consumer electronic devices), which facilitates such usage.

Typically the accelerometer and/or gyroscopes will provide a three-dimensional vector that can be incorporated in the determination of an appropriate reaction in the partial or complete activation of the smart fabric assembly. The movement sensing means enable the detection of forces/movement, and upon receipt of one or more output signals generated and communicated to a microprocessor control means by the movement sensing means, the microprocessor control means analyzes and interprets the received signals and determines, in accordance with preprogrammed parameters and criteria, whether the output signals are indicative of a condition requiring a change in all or part of the configuration of the smart fabric.

In the event that the microprocessor determines that a response is appropriate, the microprocessor activates, deactivates or dynamically controls any portions of the smart fabric assembly through changes in the electromagnets causing engagement between coupling devices.

The microprocessor may be programmed with specific parameters and criteria that are refined and nuanced for the particular needs of the wearer and/or activity. The typical algorithm for calculation of net force vectors follows the Pythagorean Theorem: if the acceleration in three-dimensions has a value of x for the vertical (up-down) axis, y for the horizontal (left-right) axis, and z for the horizontal (forward-back) axis, then the formula for net acceleration (n) is expressed as $n^2=x^2+y^2+z^2$. The absolute value of a net acceleration that exceeds certain parameters, and/or certain limits on the individual parameters, will trigger the device to immobilize. There may also be individual customized settings for the duration and strength of the immobilization force applied. In general, vertical translation is less well tolerated than lateral movements, so these parameters may typically have lower thresholds for activation.

Insulated flexible wires and/or thin sheet micro-connectors carry the electric current, as well as the output signals generated by movement sensors to the microprocessor and the electronic signals to the movement resisting means. The smart fabric could also incorporate a wireless distress signal generating mechanism, operable to notify emergency crews in the event of the deployment of the device. There are multiple component part interfaces, each of which is separately charged from the battery; consequently, the smart fabric may also be provided with an alarm mechanism to provide a warning sound/signal if any contacting interfaces are dysfunctional.

The present invention envisages use of garments or other suitable products utilizing smart fabrics of the present invention. The material could be activated by application of an appropriate stimulus, such as a current, a change in current, or the stopping of the current; such that the smart fabric is caused to "freeze" in its current state, position or shape, or which demonstrates variable rigidity to provide resistance to movement. The tensile properties within one or more regions of the fabric being altered in response to the stimulus, which activates, deactivates or dynamically controls fabric hardening means; thereby partially or substantially hardening these regions. The stimulus and/or hardening means may be thermal, chemical, mechanical, electrical, magnetic or from another appropriate source. For example, the above mentioned products could readily be caused to harden by mimicking, in response to the movement or change in movement, the stimulus and reaction resulting from a directly impacting event.

The present invention also contemplates movement sensing means being provided on one or more locations on the smart fabric and/or other elements of the device (if applicable). The smart fabric may additionally include other sensors. For example, researchers have found that molecules of a material that reacts with human serum albumin can be added (coated on) to the fibers of the fabric; which molecules detect the presence, location and intensity of bleeding (on application of an electric current through the fibers and measuring the changing conductivity across the fabric). Other sensors may also be included on the smart fabric, being a capable of monitoring the physical condition or heath of the wearer, including the heart rate, body temperature and blood pressure etc. All of this information may be communicated directly or wirelessly to emergency personnel that respond to an injury inflicted on wearer in order to assist them in the appropriate care and treatment.

The smart fabric will likely have some radiographic signature upon imaging (X-rays etc.), but given the current technology in flexible circuitry, this should have minimal impact (wires are small, while the majority of the device will be radiolucent) upon imaging of body anatomy. Material are available that are relatively rigid, but radiolucent (plastic, carbon fiber and low density alloys like magnesium are applicable). Different materials may be selected for different parts or for different places on the smart fabric, based on the weight of the device and the radiographic impact. For example, maximum radiographic importance is typically focused on the middle of a wearer in anterior and lateral projections, and some regions may be larger and bear more load than others. Radio-opaque materials such as the battery case and microprocessor unit may be positioned in regions of the body that are less critical in an emergency room situation.

In another embodiment of the invention, simplified coupling devices are provided, which when interconnected with one or more other coupling devices form a simple flexible fabric. Like the electromagnetic coupling device, each simplified coupling device has a device body, at least one tongue member protruding from the device body, and one or more tongue member receiving means provided on or defined by the device body. The tongue member of a second coupling device may be accommodated within the receiving means of the device body and is at least partially flexible relative to the device body and/or at least partially moveable within the receiving means. However, the simplified coupling device does not have engagement means, such as pins, and does not have operable electromagnets. Instead, simple retaining means are provided on the tongue members and/or on the receiving means, the retaining means being operable to afford movement of the tongue member in the corresponding receiving means within predefined spacial limits, but preventing the tongue member from decoupling from the receiving means in use. The interconnected coupling devices are thereby separable and rotatable relative to the others within the limits afforded by the retaining means and in combination forming a flexible fabric assembly which may provide a layer of protection to a wearer or device. As above, the coupling devices may be formed of meta-materials, smart materials, nano-materials, memory materials etc. and provide some hardening or other response upon subjection to certain external stimulus.

Figure 13A:
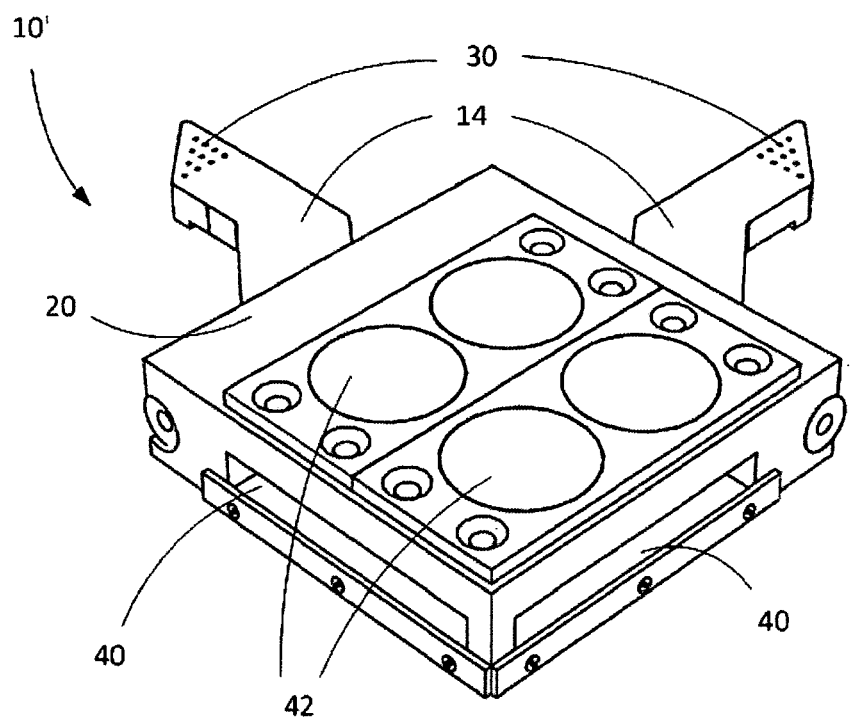
FIG. 13a shows an alternate manifestation of the electromagnetic coupling device of the present invention.
Figure 13B:
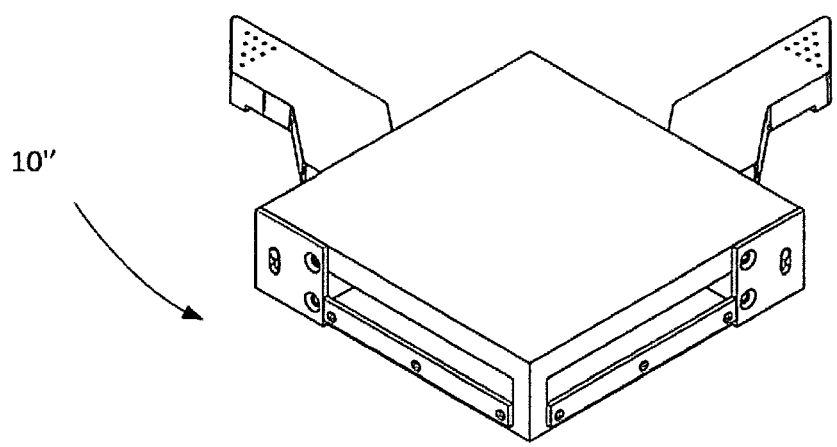
Figure 14A:
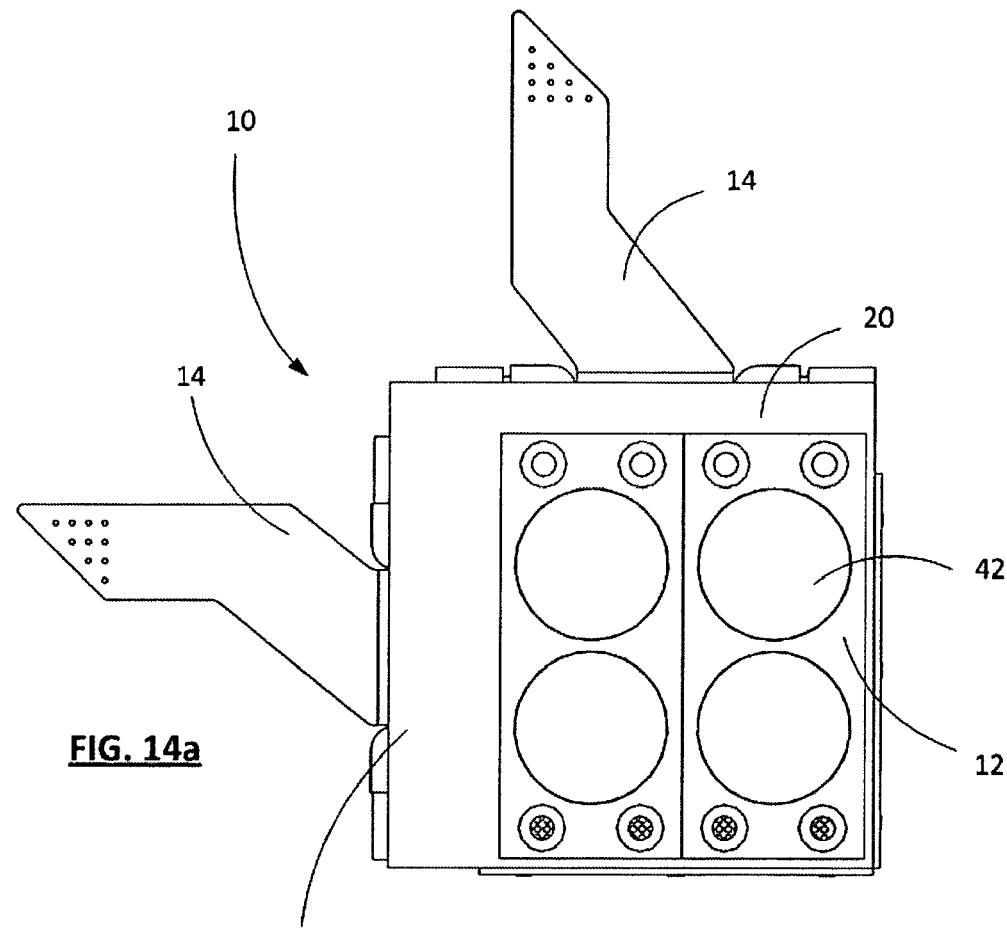
FIGS. 14a and 14b show views of the alternate coupling devices, corresponding to those shown in FIGS. 2a and 2b.
Figure 14B:
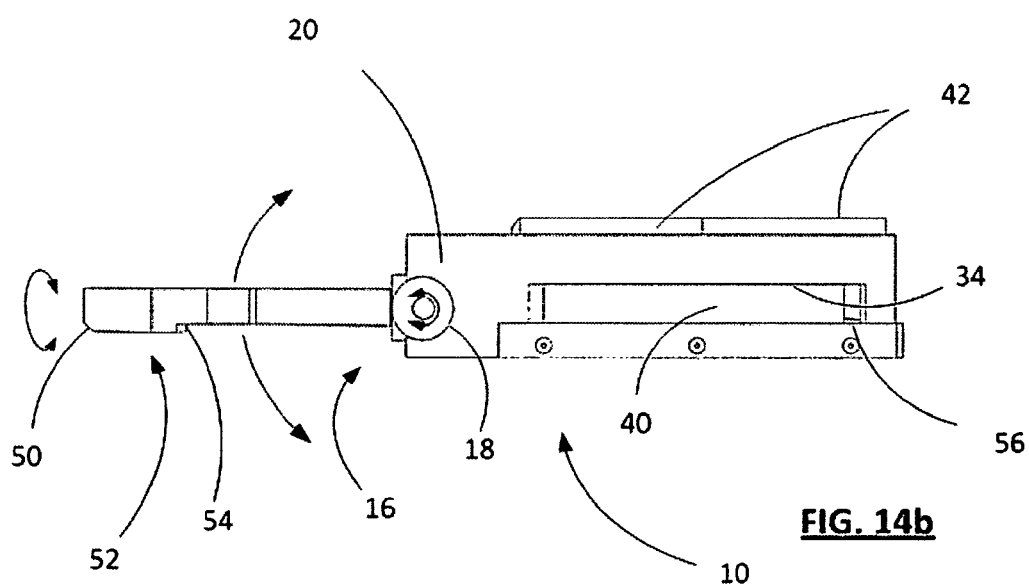

FIGS. 13*a* and 13*b* show alternate manifestations of the present invention. A modified electromagnetic coupling device 10' is shown in FIG. 13*a*, and a free moving car 10"

is shown in FIG. 13b, where engagement means 30' are provided but there are no magnets. FIGS. 14a and 14b correspond to FIGS. 2a and 2b of the earlier described electromagnetic devices. FIG. 15a shows an assembly 70' formed of the electromagnetic coupling devices (which could have included one or more free moving cars), where one casing has been removed to show the position of the connected tongue members. FIG. 15b is a side view of the assembly, and the illustrations in FIG. 15c show the assembly being flexed in different orientations (with each tongue member having a free range of movement of up to 15 degrees).

Reference is made in this specification to the application of microprocessors that may be used in accordance with the present invention and as applied in some example embodiments. It should be appreciated that the microprocessors may operate as a standalone device or may be connected (e.g., networked) to other microprocessors, computers or devices. In a networked deployment, the microprocessors may operate in the capacity of a server or a client machine in a server-client network environment, or as a peer machine in a peer-to-peer (or distributed) network environment. The microprocessor may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while a single microprocessor may be described, a single microprocessor shall also be taken to include any collection of microprocessors that individually or jointly execute a set (or multiple sets) of instructions to perform any one or more of the functions described in this specification.

Machine-readable media may be provided, on which is stored one or more sets of instructions (e.g., software, firmware, or a combination thereof) embodying any one or more of the functions described in this specification. The instructions may also reside, completely or at least partially, within the main memory, the static memory, and/or within the processor during execution thereof by the computer system. The instructions may further be transmitted or received over a network via the network interface device.

In example embodiments, a microprocessor may be configured to perform certain operations. In other embodiments, the device may include dedicated circuitry or logic that is permanently configured (e.g., within a special-purpose processor) to perform certain operations. It may also comprise programmable logic or circuitry (e.g., as encompassed within a general-purpose processor or other programmable processor) that is temporarily configured by software to perform certain operations. It will be appreciated that the decision to implement the device mechanically, in the dedicated and permanently configured circuitry, or in temporarily configured circuitry (e.g. configured by software) may be driven by cost and time considerations. Accordingly, the term "microprocessor" should be understood to encompass a tangible entity, be that an entity that is physically constructed, permanently configured (e.g., hardwired) or temporarily configured (e.g., programmed) to operate in a certain manner and/or to perform certain operations described herein.

The invention claimed is:

1. An electromagnetic coupling device, the coupling device comprising:
a device body;
a first tongue member protruding from the device body, the first tongue member having a first ferro-magnetic engagement means provided thereon;
a tongue member receiving means provided on or defined by the device body; and
an electromagnet provided substantially adjacent the tongue member receiving means;
wherein a second ferro-magnetic engagement means provided on a second tongue member of a second electromagnetic coupling device may be accommodated within the tongue member receiving means of the device body, and
wherein the electromagnet is operable to cause the second ferro-magnetic engagement means to substantially resist movement of the second tongue member within the tongue member receiving means.

2. The electromagnetic coupling device of claim 1, wherein the first tongue member is hingedly connected to the device body.

3. The electromagnetic coupling device of claim 1, wherein a textured surface is provided within the tongue member receiving means to provide enhanced frictional contact between the second ferro-magnetic engagement means and the tongue member receiving means.

4. The electromagnetic coupling device of claim 1, wherein the second ferro-magnetic engagement means is housed within locking recesses provided on the second tongue members and is biased to remain within the locking recesses unless the electromagnet is activated.

5. The electromagnetic coupling device of claim 1, wherein the second ferro-magnetic engagement means is housed within locking recesses provided on the second tongue member, biased outwardly from the locking recesses, and retractable within the locking recesses upon activation of the electromagnet.

6. The electromagnetic coupling device of claim 1, wherein a resistance of movement may be varied via a change in a magnetic force applied by the electromagnet.

7. A coupling device, the coupling device comprising:
a device body;
a first tongue member protruding from the device body; and
a receiver provided on or defined by the device body;
wherein a second tongue member of a second coupling device may be accommodated within the receiver of the device body, and
wherein the second tongue member is at least partially flexible relative to the device body and/or at least partially moveable within the receiver, and
wherein the second tongue member is mechanically engaged with the receiver.

8. The coupling device of claim 7, wherein a textured surface is provided within the receiver to provide enhanced frictional contact between the second tongue member and the receiver.

9. The coupling device of claim 7, wherein a retaining component is provided on the second tongue member and/or on the receiver; the retaining component being operable to both afford movement of the second tongue member in the receiver within predefined spatial limits and prevent the second tongue member from decoupling from the receiver; wherein the coupling device and the second coupling device are thereby separable and rotatable relative to each other within the predefined spatial limits afforded by the retaining component.

10. The coupling device of claim 7, wherein a hole or dimple is provided within the receiver to lock an engagement component.

11. The coupling device of claim 10, wherein the engagement component is housed within a locking recess provided on the first tongue member until activation.

12. The coupling device of claim 10, wherein the engagement component is hingedly connected to the first tongue member and biased to remain attached on the first tongue member until activation.

13. The coupling device of claim 10, wherein the engagement component is mechanically, pneumatically or hydraulically manipulated into or out of engagement with tongue member receiver.

* * * * *